(12) United States Patent
Guth et al.

(10) Patent No.: US 7,416,869 B2
(45) Date of Patent: Aug. 26, 2008

(54) ENZYME DELIVERY SYSTEMS, APPLICATION IN WATER BASED PRODUCTS

(75) Inventors: Jacob Guth, Upper Black Eddy, PA (US); Vickie Lentner, Hunterdon, NJ (US)

(73) Assignee: Lonza Ltd., Basel (CH)

( * ) Notice: Subject to any disclaimer, the term of this patent is extended or adjusted under 35 U.S.C. 154(b) by 411 days.

(21) Appl. No.: 10/922,790

(22) Filed: Aug. 19, 2004

(65) Prior Publication Data

US 2005/0163740 A1    Jul. 28, 2005

(51) Int. Cl.
- *C12N 11/04* (2006.01)
- *C12N 9/96* (2006.01)
- *C12N 9/02* (2006.01)
- *A61K 8/66* (2006.01)
- *A61K 8/02* (2006.01)

(52) U.S. Cl. .................. 435/188; 424/70.14; 424/94.1; 424/401; 424/455; 435/182; 435/189; 435/198; 435/226

(58) Field of Classification Search ....................... None
See application file for complete search history.

(56) References Cited

U.S. PATENT DOCUMENTS

| 5,830,449 | A | 11/1998 | Afriat et al. |
| 5,935,559 | A | 8/1999 | Afriat et al. |

*Primary Examiner*—Herbert J Lilling
(74) *Attorney, Agent, or Firm*—Darby & Darby

(57) ABSTRACT

Aqueous enzyme delivery systems as well as aqueous cosmetics and personal care products were provided which comprise at least one stabile enzyme and a polyglycerol containing at least 15 carbons. In addition, stabile non-aqueous enzyme delivery systems which are dispersions of at least one enzyme in an non-aqueous viscous liquid as well as a methods for the treatment of human skin in recreational water applications by means of enzymes are provided.

26 Claims, No Drawings

ENZYME DELIVERY SYSTEMS, APPLICATION IN WATER BASED PRODUCTS

The present invention refers to stabile aqueous and non-aqueous enzyme delivery systems suitable as additives for cosmetics and personal care products, and to stabile aqueous cosmetics and personal care products comprising an effective amount of at least one enzyme, and to the use of enzymes in recreational water applications.

Cosmetics and personal care products are known to contain various enzymes, for example proteases, lipases or oxidases. Proteases are capable of exfoliating cells from the skin, and thus can be used to renew and moisturize the skin and to reverse the outward signs of aging of the skin. Lipases can be used to treat excessive oiliness of the skin or hair, and oxidases can be used to destroy melanin, thereby resulting in lightening of the skin or bleaching of hair.

Many enzymes quickly lose their activity in aqueous systems. Therefore it is necessary to stabilize enzymes in aqueous cosmetics or personal care products.

Various attempts have been made to stabilize enzymes, especially proteases, in aqueous cosmetic compositions.

U.S. Pat. No. 5,830,449 A describes a cosmetic composition used for cleansing and/or protecting the skin. The composition comprises at least one enzyme, for example a protease, a lipase or a lactoperoxidase, and a stabilizing system consisting of at least one polyol and at least one acrylic or methacrylic polymer. The polyols can be glycerol or a glycol such as propylene glycol or polyethylene glycol.

U.S. Pat. No. 5,935,559 A describes a cosmetic composition used for cleansing the skin or to combat drying, ageing or pigmentation of the skin. It comprises a combination of silicone oil and a polyol as the stabilizing system for maintaining the activity of water sensitive agents such as enzymes, for example proteases. The polyol can be glycerol or a glycol such as propylene or ethylene glycol.

For the preparation of cosmetics and personal care products comprising an effective amount of at least one enzyme, it is more convenient to use aqueous or non-aqueous enzyme delivery systems which are solutions, emulsions or dispersions instead of enzyme powders. Such enzyme delivery systems are easier to handle and there is less risk of inhalation.

The use of enzymes in recreational water applications has not been described so far.

It is an object of the present invention to provide stabile aqueous enzyme delivery systems suitable for preparing aqueous cosmetics or personal care products. It is also an object of the present invention to provide stabile aqueous cosmetics or personal care products comprising an effective amount of at least one enzyme.

It was found that polyglycerols containing at least 15 carbon atoms have an enhanced stabilizing effect on enzymes in aqueous enzyme delivery systems compared to the stabilizing effect of glycerol.

The aqueous enzyme delivery system of the present invention comprises at least one enzyme and a polyglycerol containing at least 15 carbon atoms.

The enzyme can be a hydrolase (EC 3), an oxidoreductase (EC 1) or a mixture comprising a hydrolase and/or oxidoreductase. Examples of hydrolases are lipases, esterases, amylases, cellulases and proteases. Examples of oxidoreductases are oxidases and peroxidases.

Preferably, the enzyme is selected from the group consisting of proteases, lipases, esterases and oxidases. More preferably, the enzyme is a protease. Even more preferably, the enzyme is a cysteine proteinase. Most preferably, the enzyme is papain and/or bromelain.

The concentration of the enzyme in the aqueous enzyme delivery system is adjusted to render it suitable as an additive for aqueous cosmetics and personal care products. For example, the concentration of papain in the aqueous delivery system can range from 100 to 10,000 PU/mg, the concentration of bromelain can range from 1 to 1,000 GDU/g, the concentration of glucose oxidase can range from 500 to 1,000 GO/g and the concentration of lipase can range from 100 to 10,000 LU/g.

A proteolytic unit (PU) is defined as the quantity of enzyme which liberates one microgram of tyrosine per hour. A gelatin digestion unit (GDU) is defined as the quantity of enzyme which liberates 1 mg of amino nitrogen from standard gelatin at pH 4.5 or 5.5 after 20 minute. A lipase Unit (LU) is determined by hydrolysis ofp-nitrophenyl butyrate to nitrophenol by the lipase and measuring the rate of absorbance at a given time and comparing it to a standard. A glucose oxidase titrimetric unit of activity (GO) is the quantity of enzyme that will oxidize 3 mg of glucose to gluconic acid in 50 minutes at 35° C.

A polyglycerol containing at least 15 carbon atoms can be a single compound or a mixture thereof. Examples of polyglycerols containing at least 15 carbon atoms are pentaglycerol, hexaglycerol, heptaglycerol, octaglycerol, nonaglycerol and decaglycerol.

Preferably, the polyglycerol contains at least 21 carbon atoms, more preferably at least 27 carbon atoms, and even more preferably at least 30 carbon atoms. Most preferably the polyglycerol is decaglycerol.

The aqueous enzyme delivery system can also comprise antimicrobial agents such as Geogard® 361 and Natrulon® PC-15.

In one embodiment the aqueous enzyme delivery system additionally comprises a polyol. The polyol can be a monomeric polyol containing maximal 6 carbon atoms or a polymeric glycol. Examples of polyols containing maximal 6 carbon atoms are glycerol, ethylene glycol, propylene glycol, butylene glycol and sorbitol. Examples of polymeric glycols are polyethylene glycol 200 and 400.

Preferably, the ratio of polyglycerol/polyol is at least 1:10 (weight/weight), more preferably the ratio of polyglycerol/polyol is at least 1:1 (weight/weight). Most preferably the ratio is greater than 5:1 (weight/weight).

The aqueous enzyme delivery system can be a solution, a water-in-oil emulsion or an oil-in-water emulsion.

In a preferred embodiment the aqueous enzyme delivery system forms a solution. Preferably, the total content of polyglycerol and optional polyol in the aqueous enzyme delivery system which forms a solution is at least 40% by weight. More preferably it is at least 60% by weight. Most preferably, it is 80% by weight.

In a second preferred embodiment the aqueous enzyme delivery system additionally comprises a water-immiscible liquid and forms a water-in-oil emulsion. The water-immiscible liquid can be a viscous fatty acid ester, a viscous hydrocarbon such as a mineral oil, a synthetic oil such as a silicone oil or mixtures thereof. An example of a viscous fatty acid ester is Aldo® MCT which is a mixed esters of glycerol with caprylic and capric acids. Preferably the total content of polyglycerol and polyol in the aqueous enzyme delivery system which forms a water-in-oil emulsion is at least 5% by weight. More preferably it is at least 7% by weight. Most preferably it is 10% by weight. The aqueous enzyme delivery system which forms a water-in-oil emulsion can also comprise a thickener such as Novemer® EC-1, and emulsifiers such as Lonzest® MSA which is glycerol monostearate, Lonzest® SMS which is sorbitol monostearate or Pegosperse 1750 MS which is polyethylene glycol monostearate.

Also parts of the invention are the following methods and processes:

A method for stabilizing an enzyme in aqueous enzyme delivery systems by means of a polyglycerol containing at least 15 carbon atoms.

A process for preparing aqueous cosmetic or personal care products in form of solutions comprising an effective amount of at least one enzyme including the step of adding the aqueous enzyme delivery system of the present invention which forms a solution to a cosmetic or personal care product. Examples of aqueous cosmetic or personal care products which form solutions are shower gels and shampoos.

A method for human skin treatment in recreational water applications by means of the aqueous enzyme delivery systems of the present invention which form a solution. Examples of recreational water applications are hot tubs, spas, pools, therapeutic baths/pools, hydrotherapeutic systems, foot baths and Jacuzzi® whirl pools. An aqueous enzyme delivery system suitable for recreational water applications can additionally comprise herbal extracts and/or essential oils.

A process for preparing aqueous cosmetic or personal care products in form of emulsions, preferably oil-in-water emulsions, comprising an effective amount of at least one enzyme including the step of adding the aqueous enzyme delivery system of the present invention to a cosmetic or personal care product. Examples of cosmetic or personal care products which are emulsions are creams, lotions, blushes, foundations, sunscreens, lighteners, tanners and make-ups.

It is also an object of the present invention to provide stabile aqueous cosmetic or personal care products comprising an effective amount of at least one enzyme.

This object is achieved by the aqueous cosmetic or personal care products of the present invention comprising an effective amount of an enzyme and a polyglycerol containing at least 15 carbon atoms.

It was found that polyglycerols containing at least 15 carbon atoms have an enhanced stabilizing effect on enzymes in aqueous cosmetic and personal care products compared to the stabilizing effect of glycerol. In addition, aqueous cosmetic and personal care products comprising an effective amount of a protease and a polyglycerol containing at least 15 carbon atoms show an enhanced moisturizing effect on human skin compared to those aqueous cosmetic and personal care products comprising glycerol.

Examples of aqueous cosmetic and personal care products are bath and cleansing products such as shower gels, shampoos, soaps, after-bath products such as skin softeners, callus removers, exfoliators, skin lighteners, skin creams and lotions such as for use on the hands, face or knees to smooth, condition, mitigate wrinkles, lighten, tan, or protect from environmental insult, make-up removal products, massage creams and lotions and color cosmetics such as blushes, foundations, make-up and eye make-up.

In one embodiment, the aqueous cosmetics or personal care products can also additionally comprise a polyol.

The definitions and preferences given above for the enzyme, the polyglycerol and the polyol of the aqueous enzyme delivery system also apply to the enzyme, the polyglycerol and the polyol of the aqueous cosmetic and personal care products of the present invention.

The aqueous cosmetics and personal care products can be in any suitable form such as in form of a solution, a water-in-oil emulsion or an oil-in-water emulsion.

Preferably, the aqueous cosmetic or personal care product of the present invention is combined with a water-immiscible liquid and forms an oil-in-water emulsion.

The definitions of the water-immiscible liquid given above apply also to the aqueous cosmetic and personal care products of the present invention.

Preferably, the total content of polyglycerol and optional polyol is at least 7%, more preferably at least 10% and most preferably at least 15%.

Also parts of the invention are the following methods:

A method for treatment of the human skin by means of an aqueous cosmetic or personal care product of the present invention. Preferably, an aqueous cosmetic or personal care product of the present invention is used which comprises a protease and the skin treatment involves exfoliating and moisturizing the skin.

A method for stabilizing an enzyme in an aqueous cosmetics or personal care product by means of a polyglycerol containing at least 15 carbon atoms.

It is a yet another object of the present invention to provide non-aqueous enzyme delivery systems suitable as additives for aqueous cosmetic or personal care products which form emulsions as well as for non-aqueous cosmetic or personal care products.

The non-aqueous enzyme delivery system of the present invention is a dispersion of at least one enzyme in a non-aqueous viscous liquid.

The definitions and preferences given above for the enzyme of the aqueous enzyme delivery system also apply to the enzyme of the non-aqueous delivery system.

Examples of non-aqueous viscous liquids are viscous hydrocarbons such as mineral oils, synthetic oils such as a silicone oils, esters such as fatty acid esters, alcohols such as polyethoxylated sorbitol and amines such as polyethylenimine.

Preferably, the non-aqueous viscous liquid is a mineral oil such as Versagel® M-200.

Also parts of the invention are the following processes:

A process for preparing aqueous cosmetic or personal care products in form of emulsions, preferably of oil-in-water emulsions, wherein the products comprise an effective amount of at least one enzyme including the step of adding a non-aqueous enzyme delivery system of the present invention to an aqueous cosmetic or personal care product. Examples of aqueous cosmetic or personal care products in form of emulsions are given above.

A process for preparing non-aqueous cosmetics or personal care products comprising an effective amount of at least one enzyme including the step of adding a non-aqueous enzyme delivery system of the present invention to an non-aqueous cosmetic or personal care product. Examples of non-aqueous cosmetics and personal care products are make-up removal products, body oils and bath oils It is also an object of the present invention to provide a method for treatment of the human skin in recreational water applications.

The method of the present invention comprises the treatment of human skin in recreational water application by means of enzymes.

Examples of recreational water applications are given above. Preferred recreational water applications are spas and hot tubs.

The definitions and preferences given above for the enzyme of the aqueous enzyme delivery system also apply to the enzyme used for treatment of the skin in recreational water applications.

Baths are usually associated with skin dryness. Surprisingly, it was found that the presence of proteases in recreational water not only prevents skin dryness but also shows excellent skin moisturizing effects.

Preferably, the method of the present invention comprises exfoliating and moisturizing of the human skin in recreational water by means of proteases.

EXAMPLE 1

Stability of Proteases in Aqueous Protease Delivery Systems in Form of Solutions Papain and bromelain were dissolved in decaglycerol/water (80/20) or glycerol/water (80/20) to a final concentration of papain (200 PU/mg) and bromelain (2.3 GDU/g). The solutions were stored at 37° C. for 8 weeks. The activity of the proteases was determined by casein digestion after 2 days and after 1, 2, 4, 6 and 8 weeks. The results are shown in Table 1. The stability of the proteases in decaglycerol/water (80/20) was superior to that in glycerol/water (80/20).

TABLE 1

Stability of proteases in aqueous delivery systems which form solutions

| Aqueous delivery system | Remaining activity after days/weeks of storage [%] | | | | | |
|---|---|---|---|---|---|---|
| | 2 days | 1 wk | 2 wks | 4 wks | 6 wks | 8 wks |
| Glycerol/water (80/20) | 100 | 100 | 99.8 | 89.5 | 86.6 | 85.6 |
| Decaglycerol/water (80/20) | 100 | 99.9 | 99.7 | 98.3 | 97.0 | 96.7 |
| Water (unstabilized control) | 9.4 | nd | nd | nd | nd | nd |

Abbreviations: wk = week; nd = not detected.

EXAMPLE 2

The Preparation of a Skin Exfoliating and Moisturizing Cream which is an Oil-in-Water Emulsion by Means of an Aqueous Protease Delivery System in Form of a Solution Formulation 1: Skin Exfoliating and Moisturizing Cream

| Ingredient | [% (w/w)] |
|---|---|
| Phase 1 | |
| Lonzest ® SMS | 2.25 |
| Aldo ® MCT | 10.00 |
| Lonzest ® MSA | 1.50 |
| Pegosperse ® 1750 MS | 0.75 |
| Phase 2 | |
| Urea | 10.00 |
| Decaglycerol | 7.00 |
| Butylene glycol | 3.00 |
| Water | 61.75 |
| Phase 3 | |
| Geogard ® 361 | 0.25 |
| Novemer ® EC-1 | 0.50 |
| Phase 4 | |
| Papain (200 PU/mg) and Bromelain (2.3 GDU/g) | 3.00 |

Phase 1 was heated to 80° C. and added to a vigorously stirred phase 2 at 80° C. The obtained mixture was stirred vigorously at 80° C. for 1 h and was slowly cooled to below 40° C. with stirring. Phase 3 was slowly added. The pH of the mixture was adjusted to 5.8 and the aqueous enzyme delivery system of example 1 which is a solution of papain (200 PU/mg) and bromelain (2.3 GDU/g) in decaglycerol/water (80/20) was added.

EXAMPLE 3

Stability of Proteases in a Skin Exfoliating and Moisturizing Cream

The skin exfoliating and moisturizing cream of formulation 1 (Example 2) comprising 7% by weight decaglycerol and a control cream which was identical to the one of formulation 1, except that it contained glycerol instead of decaglycerol, were stored at 37° C. for 8 weeks. The activity of the proteases was determined by casein digestion after 1, 2, 4, 6 and 8 weeks. The results are shown in Table 2. The stability of the proteases in the cream of formulation 1 was superior to the one in the control cream.

TABLE 2

Stability of proteases in a skin exfoliating and moisturizing cream

| Skin exfoliating/moisturizing cream comprising | remaining activity after weeks of storage [%] | | | | |
|---|---|---|---|---|---|
| | 1 wk | 2 wks | 4 wks | 6 wks | 8 wks |
| 7% by weight glycerol | 100 | 99.3 | 96.7 | 87.9 | 85.2 |
| 7% by weight decaglycerol | 100 | 99.5 | 99.0 | 97.0 | 96.0 |

EXAMPLE 4

Human Skin Exfoliating/Moisturizing Effect of the Cream of Formulation 1 (Example 2)

Human skin was treated with the cream of formulation 1 and with control creams which were identical to the cream of formulation 1, except that decaglycerol was substituted by glycerol, except that no proteases were included or except that decaglycerol was substituted by glycerol and no proteases were included. The skin was treated with the cream once a day for 11 days and the conductivity of the skin surface was measured every day before the treatment. Proteases exfoliate the outer, dead layers of the skin and simultaneously expose the underlying new and living skin cells. These new skin cells are more hydrated than exfoliated cells and as a result will conduct electricity more effectively. The results are given in Table 3.

TABLE 3

Water content of the skin surface after treatment of the skin with cream

| Skin exfoliating/moisturizing cream comprising | Water content of the skin after days of treatment [%] | | | | | | | |
|---|---|---|---|---|---|---|---|---|
| | 1 day | 2 days | 3 days | 6 days | 8 days | 9 days | 10 days | 11 days |
| Glycerol, no proteases | 41.3 | 51.4 | 52.4 | 50.9 | 54.7 | 59.4 | 55.0 | 56.0 |
| Decaglycerol, no proteases | 44.4 | 54.2 | 56.9 | 53.0 | 59.2 | 62.8 | 60.5 | 58.5 |
| Glycerol, proteases | 42.9 | 58.1 | 62.2 | 58.4 | 63.2 | 66.3 | 64.7 | 66.2 |

TABLE 3-continued

Water content of the skin surface after treatment of the skin with cream

| Skin exfoliating/ moisturizing cream comprising | Water content of the skin after days of treatment [%] | | | | | | | |
|---|---|---|---|---|---|---|---|---|
| | 1 day | 2 days | 3 days | 6 days | 8 days | 9 days | 10 days | 11 days |
| Decaglycerol, proteases | 42.6 | 60.4 | 65.5 | 63.3 | 67.9 | 72.1 | 70.2 | 71.9 |
| Untreated skin (control) | 38.2 | 41.8 | 44.6 | 44.1 | 43.8 | 45.0 | 43.9 | 43.4 |

EXAMPLE 5

Use of Proteases for Moisturizing the Human Skin in Recreational Water Applications Human skin was soaked 15 min under simulated spa conditions, namely in water comprising 0.04 PU/mg of papain and 6 ppm $Br_2$ added as a disinfectant at 40° C. The water content of the skin was determined one hour after the 15 min soak by measuring its conductivity. 5 Hours after the first 15 min soak the skin was again soaked for 15 min under the same simulated spa conditions, and the water content of the skin was determined 16 hours after the second 15 min soak. As a control the water content of skin soaked under the same conditions, but without proteases present, was also determined. The results are given in Table 4.

TABLE 4

Water content of skin after treatment of the skin with water comprising proteases

| Water comprising | change in water content of the skin compared to the water content of the skin before treatment [%] | |
|---|---|---|
| | 1 h after the first 15 min soak | 16 h after the second 15 min soak |
| no proteases | −6.8 | −12.2 |
| proteases | 15.8 | 26.0 |

EXAMPLE 6

Preparation of an Aqueous Protease Delivery System Suitable for Hot Tubs

Formulation 2: Aqueous Protease Delivery System Suitable for Hot Tubs

| Ingredient | [% (w/w)] |
|---|---|
| Decaglycerin | 80.00 |
| Papain (62,000 PU/g) | 2.80 |
| Bromelain (33,000 GDU/g) | 0.10 |
| Herbal extracts | 0.10 |
| Essential oils | 0.50 |
| Water | 16.25 |
| Geogard ® 361 | 0.25 |

A solution of papain and bromelain in water was added to decaglycerol. The pH was adjusted to 6.4 and the herbal extracts, essential oils and Geogard® 361 were added.

EXAMPLE 7

Preparation of an Aqueous Protease/Lipase Delivery System Suitable for Hot Tubs or Spas Formulation 3: Aqueous Protease/Lipase Delivery System Suitable for Use Hot Tubs and Spas

| Ingredient | [% (w/w)] |
|---|---|
| Decaglycerin | 80.00 |
| Papain (62,000 PU/g) | 2.80 |
| Bromelain (33,000 GDU/g) | 0.10 |
| Lipase (100 L = 500 LU/g) | 0.50 |
| Herbal extracts | 0.10 |
| Borax | 0.50 |
| Essential oils | 0.50 |
| Water | 15.75 |
| Geogard ® 361 | 0.25 |

Borax was added to a solution of papain, bromelain and lipase in water. This solution was added to decaglycerol. The pH was adjusted to 6.4 and the herbal extracts, essential oils and Geogard® 361 were added.

EXAMPLE 8

Preparation of a Skin Lightening Cream Comprising Decaglycerol and an Effective Amount of Oxidase Formulation 4: Skin Lightening Cream

| Ingredient | [% (w/w)] |
|---|---|
| Phase 1 | |
| Stearic acid | 3.00 |
| Butyl methoxydibenzylmethane | 0.50 |
| Octyl p-methoxycinnamate | 2.00 |
| Mineral oil | 1.50 |
| Cetyl alcohol | 1.00 |
| Lonzest ® 143-S | 1.50 |
| Aldo ® MCT | 1.50 |
| Lonzest ® MSA | 1.50 |
| Pegosperse ® 1750 MS | 0.75 |
| Lonzest ® SMS | 2.25 |
| Phase 2 | |
| Urea | 3.00 |
| Butylene glycol | 3.00 |
| Water | 50.00 |
| Phase 3 | |
| L-Carnitine | 1.00 |
| Decaglycerol | 7.00 |
| Arbutin | 1.00 |
| Water | 17.25 |
| Geogard ® 361 | 0.25 |
| Phase 4 | |
| Glucose oxidase [500 U/g] | 2.00 |

Phase 1 was heated to 80° C. and added to vigorously stirred phase 2 at 80° C. The obtained mixture was stirred vigorously at 80° C. for 1 h and was slowly cooled to below 40° C. with stirring. Phase 3 was slowly added. The pH of the mixture was adjusted to 5.8 and phase 4 was added.

EXAMPLE 9

Preparation of an Aqueous Protease Delivery System in Form of a Water-in-Oil Emulsion Composition 1: Aqueous Protease Delivery System in Form of a Water-in-Oil Emulsion

| Ingredient | [% (w/w)] |
|---|---|
| Phase 1 | |
| Aldo ® MCT | 40.00 |
| Pegosperse ® 1750 MS | 1.50 |
| Lonzest ® MSA | 3.00 |
| Lonzest ® SMS | 5.00 |
| Phase 2 | |
| Decaglycerol | 7.00 |
| Water | 42.00 |
| Phase 3 | |
| Novemer ® EC-1 | 1.00 |
| Phase 4 | |
| Geogard ® 361 | 0.50 |
| Phase 5 | |
| Papain and Bromelain | |

Phase 1 was heated to 80° C. and added to a vigorously stirred phase 2 at 80° C. The obtained mixture was stirred vigorously at 80° C. for 1 h and was slowly cooled down to below 40° C. with stirring. Phases 3 and 4 were slowly added. The pH of the emulsion was adjusted to 5.8 and powders of papain and bromelain were added to reach a final activity of 200 PU/mg and 2.3 GDU/g, respectively.

EXAMPLE 10

Stability of Proteases in Aqueous Proteases Delivery Systems in Form of Water-in-Oil Emulsions The protease delivery system of Example 9 was stored at 37° C. The activity of the proteases was determined by casein digestion after 2 days and after 1, 2, 4, 6 and 8 weeks. Control emulsions which were identical to the one of example 9, but which either included glycerol instead of decaglycerol or did not include a stabilizer at all were also stored at 37° C. In addition, solutions of papain and bromelain in decyglacrol/water (7/93) or glycerol/water (7/93) were also stored at 37° C. as controls. The results are shown in Table 5. The stability of the proteases in the protease delivery system of Example 9 was superior to that of the controls.

TABLE 5

Stability of proteases in various aqueous protease delivery systems

| Aqueous protease delivery system | Remaining activity of the enzymes after days/weeks of storage [%] | | | | | |
|---|---|---|---|---|---|---|
| | 2 days | 1 wk | 2 wks | 4 wks | 6 wks | 8 wks |
| Emulsion, no stabilizer | 100 | 100 | 76.9 | 68.7 | 63.2 | 42.6 |
| Emulsion, 7% by weight glycerol | 100 | 100 | 97.4 | 92.0 | 90.0 | 85.5 |
| Emulsion, 7% by weight decaglycerol | 100 | 100 | 96.4 | 93.7 | 92.9 | 92.7 |
| Glycerol/water (7/93) | 46 | nd | nd | nd | nd | nd |
| Decaglycerol/water (7/93) | 57 | nd | nd | nd | nd | nd |

Abbreviations: wk = week; nd = not detected.

EXAMPLE 11

Preparation of an Oil Make-Up Remover Comprising an Effective Amount of Lipase by Means of an Aqueous Lipase Delivery System in Form of a Water-in-Oil Emulsion Formulation 6: An Oil Make-Up Remover Comprising an Effective Amount of Lipase

| Ingredient | [% (w/w)] |
|---|---|
| Phase 1 | |
| Octyl dimethyl amine oxide | 18.0 |
| Glycerol | 20.0 |
| Sorbitol | 20.0 |
| Urea | 5.00 |
| Geogard ® 361 | 0.4 |
| Novemer ® EC-1 | 2.0 |
| Water | 32.6 |
| Phase 2 | |
| Lipase in form of a water-in-oil emulsion [1000 LU/g] | 2.0 |

Phase 2 was added to phase 1 at pH 7.2.

EXAMPLE 12

Preparation of a Skin Lightening Cream which is an Oil-in-Water Emulsion

Composition 4: Skin Lightening Cream.

| Ingredient | [% (w/w)] |
|---|---|
| Phase 1 | |
| Stearic acid | 3.00 |
| Mineral oil | 1.50 |
| Cetyl alcohol | 1.50 |
| Lonzest ® 143-S | 1.50 |
| Lonzest ® MSA | 1.50 |
| Pegosperse ® 1750 MS | 0.75 |
| Lonzest ® SMS | 2.25 |
| Phase 2 | |
| Urea | 10.00 |
| Butylene glycol | 3.00 |
| Glycerol | 7.00 |
| Water | 65.25 |
| Phase 3 | |
| Novemer ® EC-2 | 0.50 |
| Geogard ® 361 | 0.25 |
| Fragrance | |
| Phase 4 | |
| Glucose oxidase water-in-oil emulsion [500 U/g] | 2.00 |

Phase 1 was heated to 80° C. and added to a vigorously stirred phase 2 at 80° C. The obtained mixture was stirred vigorously at 80° C. for 1 h and was slowly cooled to below 40° C. with stirring. Phase 3 was slowly added. The pH of the mixture was adjusted to 5.5 and phase 4 was added.

EXAMPLE 13

A Non-Aqueous Protease Delivery System which is a Dispersion of Proteases in Mineral Oil Papain and bromelain were dispersed in Versagel® M-200 to a final concentration of papain (200 PU/mg) and bromelain (2.3 GDU/g). The solutions were stored at 37° C. for 8 weeks. The activity of the proteases was determined by casein digestion after 2 days and after 1, 2, 4, 6 and 8 weeks. Solutions of the proteases in decaglycerol/water (80/20) and glycerol/water (80/20) were also stored at 37° C. for 8 weeks. The stability of the proteases in Versagel® M-200 was comparable to that in glycerol/water (80/20).

TABLE 6

Stability of proteases in various enzyme delivery systems

| Protease delivery system | Remaining activity after days/weeks of storage [%] | | | | | |
|---|---|---|---|---|---|---|
| | 2 days | 1 wk | 2 wks | 4 wks | 6 wks | 8 wks |
| Water (control) | 9.4 | nd | nd | nd | nd | nd |
| Versagel-M 200 | 100 | 97.3 | 93.3 | 90.8 | 87.8 | 85.1 |
| Glycerol/water (80/20) | 100 | 100 | 99.8 | 89.5 | 86.6 | 85.6 |
| Decaglycerol/water (80/20) | 100 | 99.9 | 99.7 | 98.3 | 97.0 | 96.7 |

Abbreviations: wk = week; nd = not detected.

EXAMPLE 14

Preparation of a Skin Exfoliating and Moisturizing Cream by Means of the Non-Aqueous Protease Delivery System of Example 13

Formulation 8: Skin Exfoliating/Moisturizing Cream

| Ingredient | [% (w/w)] |
|---|---|
| Phase 1 | |
| Aldo ® MCT | 20.00 |
| Pegosperse ® 1750 | 0.75 |
| Lonzest ® MSA | 1.50 |
| Lonzest ® SMS | 2.50 |
| Phase 2 | |
| Glycerol | 5.00 |
| Sorbitol | 2.00 |
| Novemer ® EC-1 | 1.00 |
| Water | 63.71 |
| Phase 3 | |
| Geogard ® 361 | 0.40 |
| Perfume | 0.14 |
| Phase 4 | |
| Dispersion of papain [200 PU/mg] and bromelain [2.3 GDU/g] in Versagel-M 200 | 3.00 |

Phase 1 was heated to 80° C. and added to a vigorously stirred phase 2 at 80° C. The obtained mixture was stirred vigorously at 80° C. for 1 h and was slowly cooled to below 40° C. with stirring. Phase 3 was slowly added. The pH of the mixture was adjusted to 5.5 and phase 4 was added.

The invention claimed is:

1. An aqueous enzyme delivery system comprising at least one enzyme and a polyglycerol containing at least 15 carbon atoms.

2. The aqueous enzyme delivery system of claim 1 wherein the enzyme is selected from the group consisting of proteases, lipases, esterases and oxidases.

3. The aqueous enzyme delivery system of claim 1 which additionally comprises a polyol.

4. The aqueous enzyme delivery system of claim 3 wherein the ratio of polyglycerol/polyol is at least 1:10 (weight/weight).

5. The aqueous enzyme delivery system of claim 1 which forms a solution.

6. The aqueous delivery system of claim 5 wherein the total content of polyglycerol is at least 40% by weight.

7. The aqueous delivery system of claim 1 which additionally comprises a water-immiscible liquid and forms a water-in-oil emulsion.

8. The aqueous delivery system of claim 7 wherein the total content of polyglycerol and optional polyol is at least 5% by weight.

9. A method for stabilizing an enzyme in an aqueous enzyme delivery system comprising the step of adding a polyglycerol containing at least 15 carbon atoms to the aqueous enzyme delivery system.

10. A process for preparing an aqueous cosmetic or personal care product in the form of a solution comprising an effective amount of at least one enzyme, the process comprising the step of adding an aqueous enzyme delivery system of claim 5 to a cosmetic or personal care product.

11. A process for preparing an aqueous cosmetic or personal care product in the form of a solution comprising an effective amount of at least one enzyme, the process comprising the step of adding an aqueous enzyme delivery system of claim 6 to a cosmetic or personal care product.

12. A method for treating human skin in a recreational water application comprising an aqueous enzyme delivery system of claim 5 to the water of the recreational water application.

13. A method for treating human skin in a recreational water application comprising an aqueous enzyme delivery system of claim 6 to the water of the recreational water application.

14. A process for preparing an aqueous cosmetic or personal care product in the form of an emulsion comprising an effective amount of at least one enzyme comprising the step of adding an aqueous enzyme delivery system of claim 5 to a cosmetic or personal care product.

15. The process of claim 14 wherein the cosmetic and personal care product is an oil-in-water emulsion.

16. An aqueous cosmetic or personal care product comprising an effective amount of at least one enzyme and a polyglycerol containing at least 15 carbon atoms.

17. The aqueous cosmetic or personal care product of claim 16 wherein the enzyme is selected from the group consisting of proteases, lipases, esterases and oxidases.

18. The aqueous cosmetic or personal care product of claim 16 which additionally comprises a polyol.

19. The aqueous cosmetic or personal care product of claim 18 wherein the ratio of polyglycerol/polyol is at least 1:10 (weight/weight).

20. The aqueous cosmetic or personal care product of claim 16 which is an oil-in-water emulsion.

21. The aqueous cosmetic or personal care product of claim 20 wherein the total content of polyglycerol and optional polyol is at least 7% by weight.

22. A method for treatment of human skin comprising applying an aqueous cosmetic or personal care product of claim 16 to the skin.

23. The method of claim 22 wherein the enzyme is a protease and the skin is exfoliated and moisturized.

24. A method for stabilizing an enzyme in an aqueous cosmetic or personal care product comprising the step of adding a polyglycerol containing at least 15 carbon atoms to the product.

25. The aqueous delivery system of claim 5 wherein the total content of polyglycerol is at least 60% by weight.

26. The aqueous delivery system of claim 5 wherein the total content of polyglycerol is at least 80% by weight.

* * * * *